(12) United States Patent
Kosierkiewicz (10) Patent No.: US 9,113,802 B2
(45) Date of Patent: Aug. 25, 2015

(54) METHOD OF STIMULATING AND RECORDING FROM ULNAR DORSAL CUTANEOUS SENSORY NERVE

(76) Inventor: Tomasz Andrzej Kosierkiewicz, Mount Vernon, IL (US)

( * ) Notice: Subject to any disclaimer, the term of this patent is extended or adjusted under 35 U.S.C. 154(b) by 729 days.

(21) Appl. No.: 12/501,454

(22) Filed: Jul. 12, 2009

(65) Prior Publication Data

US 2011/0009768 A1    Jan. 13, 2011

(51) Int. Cl.
*A61B 5/05* (2006.01)
*A61B 5/04* (2006.01)
*A61N 1/00* (2006.01)
*A61B 5/11* (2006.01)
*A61B 5/00* (2006.01)

(52) U.S. Cl.
CPC ........... *A61B 5/04001* (2013.01); *A61B 5/6848* (2013.01); *A61B 5/1104* (2013.01); *A61B 5/4528* (2013.01); *A61B 5/4893* (2013.01); *A61B 5/68* (2013.01); *A61B 5/6801* (2013.01); *A61B 5/6824* (2013.01); *A61B 5/6825* (2013.01)

(58) Field of Classification Search
CPC ............. A61B 5/04001; A61B 5/1104; A61B 5/4893; A61B 5/68; A61B 5/6801; A61B 5/6824; A61B 5/6825
USPC ........ 600/382, 384, 546, 547, 554; 607/2, 46, 607/48, 115, 145
See application file for complete search history.

(56) References Cited

U.S. PATENT DOCUMENTS

| | | | |
|---|---|---|---|
| 6,553,245 B1* | 4/2003 | Grace et al. | 600/375 |
| 2007/0129771 A1* | 6/2007 | Kurtz et al. | 607/48 |
| 2007/0149892 A1* | 6/2007 | Guldalian | 600/554 |

OTHER PUBLICATIONS

Leis et al. "Radial nerve cutaneous innervation to the ulnar dorsum of the hand", Clinical Neurophysiology, vol. 119, Issue 3, Mar. 2008, pp. 662-666.*
Hoffman et al. "Paired Study of the Dorsal Cutaneous Ulnar and Superficial Radial Sensory Nerves", Arch Phys Med Rehabil, vol. 69, Aug. 1988, pp. 591-594.*
"Laboratory Reference for Clinical Neurophysiology", by J. A. Liveson, published by Oxford University Press in 1992, pp. 159-161.

(Continued)

*Primary Examiner* — Devin Henson
(74) *Attorney, Agent, or Firm* — Jessica W. Smith; Loza & Loza, LLP (57) ABSTRACT

A device to stimulate and measure a response from the ulnar dorsal cutaneous nerve of a patient may include a first surface electrode to apply a stimulating signal to the ulnar dorsal cutaneous nerve, a second surface electrode to record the response from the stimulating signal after applying the stimulating signal to the ulnar dorsal cutaneous nerve, and a third surface electrode to reference the stimulating signal. The second surface electrode may be placed over the fifth metacarpal joint, and the device may include a ground electrode positioned over the dorsal surface of the hand. The device may include a inactive stimulating electrode positioned near to the first surface electrode. The inactive stimulating electrode may be positioned within 3 cm of the first surface electrode, and the first electrode may be placed substantially above the tendon the flexor carpi ulnaris muscle. The first electrode may be placed substantially at the level of styloid, and the second surface electrode may be placed in an area supplied by the ulnar dorsal cutaneous nerve. The first surface electrode may be placed substantially proximal to the styloid.

10 Claims, 7 Drawing Sheets

(56) References Cited

OTHER PUBLICATIONS

"Dorsal Cutaneous Ulnar nerve Conduction", Dae Joo Kim, M. D., from Archives of Neurology, vol. 38 May 1981 pp. 321 and 322.

"Limitation of the Clinical Utility of the Ulnar Dorsal Cutaneous Sensory Nerve Action Potential", by A. L. C. R. Dutra De Oliveira, published in Clinical Nerve Physiology 111 2000 1208-1210.

"Atlas of Electromyography", A. Arturo Leis, M. D., Vincente C. Trapani, M. D., Oxford University Press, pp. 23-28.

"The limitation of dorsal ulnar cutaneous sensory response in the patient with ulnar neuropathy at the elbow", by S. Venkatesh, M. D., published in Muscle and Nerve, Mar. 1995, 18:345-347.

"Clinical Electromyography: Nerve Conduction Studies" Shin J. Oh, M. D., pp. 45-47.

"Radial Sensory Conduction in Hand" by Henry A. Spindler, published in Archive of Physical Medicine and Rehabilitation, vol. 6, Nov. 7, 1986, pp. 821 through 823.

"Paired study of the Dorsal Cutanous Ulnar and Superficial Radial Sensory Nerves", Martin D. Hoffman, M. D., published in Archives of Physical Medicine and Rehabilitation, vol. 69, Aug. 1988, pp. 591 to 594.

"Dorsal ulnar cutaneous nerve conduction studies in asymptomatic population", by Sherry H. Young, M. D., published in Archives of Physical Medicine and Rehabilitation, vol. 81, Sep. 2000, pp. 1171 through 1172.

"Dorsal Ulnar Cutaneous Nerve Conduction, Reference Value" by Solange Garibaldi, published in Arq Neuropsiquiatr 2002; 60 (2-b): 349-352.

Ulnar nerve lesions at the wrist: new technique for recording from the sensory dorsal branch of the ulnar nerve, Joe F. Jabre, Neurology 1980; 30; 873-876.

"Radial nerve cutaneous innervation to the ulnar dorsum of the hand", Leis A, Wells K., Clin Neurophysiol. Mar. 2008;119(3):662-6.

* cited by examiner

METHOD OF STIMULATING AND RECORDING FROM ULNAR DORSAL CUTANEOUS SENSORY NERVE

FIELD OF INVENTION

This invention relates to a method used to perform sensory nerve conduction studies and to assess physiologic function of the ulnar dorsal cutaneous sensory nerve.

BACKGROUND

The dorsal cutaneous branch of the ulnar nerve is a large sensory nerve which arises from the distal third of the forearm. It carries fibers from the C8 (cervical eight nerve root), T1 (thoracic first nerve root) via the medial cord of the brachial plexus. It innervates the dorsal skin over the medial metacarpal region and the medial one and one half digits but not the terminal phalanges. The latter is innervated via palmar branches of the ulnar nerve (more specifically the superficial branch).

The course of the dorsal cutaneous nerve becomes superficial approximately 5 cm above wrist where it lies between the flexor carpi ulnaris and the ulna. The dorsal cutaneous nerve is spared in lesions at the wrist, but may be involved with more proximal lesions, for example, at the medial epicondyle or cubital tunnel.

Clinically, sensory involvement of the dorsum of the digits implies the lesion above the wrist involving the dorsal cutaneous branch which is given off in the forearm. Sensory abnormalities restricted to the skin of the hypothenar eminence and volar ulnar digits with some distal dorsal digital involvement suggest a wrist lesion implicating the superficial branch of the ulnar nerve. See, e.g., Reference 1 cited below.

Clinical and electrophysiological (sensory nerve conduction studies) evaluation of the ulnar dorsal cutaneous nerve is useful in topographical analysis of the ulnar mononeuropathies. See, e.g., References 2 and 3 cited below. The finding of preserved normal function of the ulnar dorsal cutaneous nerve is detrimental to the diagnosis of ulnar mononeuropathy at the proximal Guyon's canal.

The ulnar nerve is the main continuation of the medial cord of the brachial plexus. Its fibers are usually derived from the eight cervical and first thoracic roots although occasionally the seventh cervical root makes the contribution via the lateral cord. In the axilla the nerve runs between the axillary artery and vein. In the arm, it stays between the brachial artery and vein, sharing the neurovascular bundle with median nerve. At the midarm, it leaves the neurovascular bundle and passes posteriorly through the medial intermuscular septum to descend on the medial aspect of the medial head of the triceps. The nerve is superficial throughout its course and innervates no muscle in the arm. At the elbow, the nerve lies in the groove formed by the medial epicondyle of the humerus and the olecranon process of the ulna (the retrocondylar groove). It enters the forearm through the aponeurotic arcade (the cubital tunnel) joining the two heads of the flexor carpi ulnaris, which it innervates. The nerve travels through the belly of the flexor carpi ulnaris and then exits by piercing aponeurosis of the anterior surface of the muscle. It then lies in the plain between the flexor carpi ulnaris and flexor digitorum profundus (to digits 4 and 5), which it innervates. See, e.g., Reference 4 cited below.

The nerve is joined by the ulnar artery in the upper forearm to form a neurovascular bundle. About the middle of the forearm the ulnar nerve gives rise to the palmar cutaneous branch, which descends to provide sensory innervation to the medial aspect of the proximal palm. About 7 cm proximal to the wrist it also gives off a dorsal cutaneous branch, which provides innervation to the medial aspect of the dorsum of the hand and dorsal proximal aspect of the fifth and medial fourth digits. The ulnar nerve provides no sensory innervation above the wrist. See, e.g., Reference 4 cited below.

At the wrist, the ulnar nerve and artery lie in a canal formed by the pisiform medially and the hook of the hamate laterally (Guyon's canal). In this region the nerve divides into superficial and deep branches. Although, the superficial branch is generally considered a sensory branch, it supplies the palmaris brevis, a thin muscle beneath skin of the proximal medial palm, which cannot be studied electromyographically. It then provides sensory innervation to the distal palm and terminates into two digital branches that are distributed to the ulnar side of the fifth digit and the adjoining sides of fourth and fifth digits. The deep muscular branch gives of a hypothenar branch to innervate the abductor, opponens, and flexor digiti minimi. It then follows the course of the deep palmar arch across the hand and as it crosses it supplies dorsal and palmar interossei and third and fourth lumbricales. At its termination between the thumb and index finger it supplies the flexor pollicis brevis (deep head) and adductor pollicis. Although the ulnar nerve or its branches may be involved by penetrating injuries at any level, there are certain sites where the nerve is prone to injury. Compression neuropathies of the ulnar nerve at the elbow are common and widely recognized. In the retrocondylar groove, the nerve lies on a bone covered only by a thin layer of skin and is subject to chronic compression from multiple etiologies. At 1-2 cm distally, the nerves may be trapped at the cubital tunnel. Compression at either side may result in the clinical presentation known as ulnar neuropathy at the elbow. Rarely, the nerve may be entrapped in the proximal forearm as it pierces the deep aponeurosis investing the undersurface of the flexor carpi ulnaris of the distal forearm by a fibrovascular band and hypertrophied flexor carpi ulnaris tendon. Entrapment at wrist (Guyon's canal) may present with a different pattern of sensory and motor deficit depending on the degree of the involvement of the superficial (sensory) or deep (motor) branches. See, e.g., Reference 4 cited below.

Ulnar Neuropathy at the Elbow (Retrocondylar Groove).

Ulnar neuropathy at the elbow can be caused by compression in the retrocondylar groove due to repeated trauma (e.g., habitual leaning on the elbows), traumatic joint deformity, distal humerus fracture, elbow dislocations, recurrent subluxations of the nerve, callus formation, rheumatic and degenerative joint disease, congenital anomalies of the medial epicondylo-olecranon ligament, valgus deformity, and immobilization during surgery.

Originally the term Tardy Ulnar Palsy referred to antecedent traumatic joint deformity or recurrent subluxation. Many clinicians now use the term for any entrapment of the ulnar nerve in the elbow. It appears that ulnar neuropathy may herald the onset of more generalized neuropathy. Ulnar neuropathy at the retrocondylar groove should be distinguished electrodiagnostically from cubital tunnel syndrome. The distinction can be important in surgical management; the former may require surgical transposition of the nerve whereas the latter may warrant simple decompression of the nerve in the tunnel without transposition. See, e.g., Reference 4 cited below.

Clinical features are paresthesia, pain, or numbness that occurs in the sensory distribution of the ulnar nerve including the dorsum of the hand. There is pain or tenderness at the elbow with weakness and wasting of the first dorsal interosseous and other ulnar innervated hand muscle that may occur in severe cases. Clinical evidence of weakness may preferentially involve the first dorsal interosseous. Weakness of the flexor carpi ulnaris and flexor digitorum profundus (to digits 4 and 5) may be variable. Radiographic studies may be reveal rheumatic, arthritic, or post-traumatic changes around the elbow. Routine nerve conduction studies may, among others, demonstrate absent or reduced ulnar dorsal cutaneous response. See, e.g., References 4 and 5 cited below.

Ulnar neuropathy of the elbow (Cubital tunnel syndrome).

Entrapment of the ulnar nerve occurs in the tunnel formed by the tendinous arch connecting the humeral and ulnar heads of the flexor carpi ulnaris one to two cm distal to the medial epicondyle. The cubital tunnel narrows when the elbows are flexed, and this is important in the development of the compression neuropathy. There is no joint deformity or prior trauma to the elbow. Bilateral ulnar neuropathy occurs frequently. Ulnar neuropathy at the retrocondylar groove should be distinguished electrodiagnostically from the cubital tunnel syndrome. As discussed above, the former generally requires surgical transposition of the nerve whereas the latter may warrant simple decompression in the tunnel without transposition.

Paresthesia, pain, and numbness occur in the sensory distribution of the ulnar nerve, including the dorsum of the hand. There is pain or tenderness at or slightly distal to the elbow. In severe cases, weakness and wasting of the first dorsal interosseous and other ulnar innervated hand muscles may occur. Clinical evidence of weakness may preferentially involve the first dorsal interosseous. Weakness of the flexor carpi ulnaris and flexor digitorum profundus (to digits four and five) may be variable. Radiographic studies are normal. Routine nerve conduction studies may, among others, demonstrate absent or reduced ulnar dorsal cutaneous response. See, e.g., Reference 4 cited below.

Ulnar neuropathy of the Wrist (Guyon's canal).

Entrapment of the ulnar nerve occurs in the tunnel formed by the pisiform bone medially and the hook of the hamate laterally. The floor consists of thick transverse carpal ligament and subjacent bone. The distal roof is rigidly bound by the piso-hamate ligament. Entrapment may be associated with a lipoma, ganglion cyst, ulnar mass lesion, or chronic compression to the hypothenar region (e.g., due to bicycle bars, crutches, or occupation).

Within the canal the nerve divides into superficial (sensory) and deep (muscular) branches.

Nerve or branch lesions in the four different locations within Guyon's canal produced distinctive patterns of symptoms and signs.

Pattern 1.

A deep branch lesion distal to the hypothenar motor branch produces weakness in the interossei and lumbricales, but not in the hypothenar muscle; and there are no sensory deficits.

Pattern 2.

A lesion at or proximal to hypothenar motor branch produces weakness in the interossei, lumbricales, and hypothenar muscles; and there are no sensory deficits.

Pattern 3.

A lesion at or proximal to bifurcation into the deep and superficial branches produces weakness in the interossei, lumbricales and hypothenar muscle and sensory deficits in the distal palm, fifth digit, and ulnar side of the fourth digit.

Pattern 4.

The lesion limited to the superficial branch produces only sensory deficit in the distal palm, fifth digit, and ulnar side of the fourth digit.

The lesion that is comprised of deep nodal branch pattern 1 and 2 may be confused with focal onset of amyotrophic lateral sclerosis particular in all-ulnar hand. The lesion that comprises of superficial branch (pattern 3 and 4) do not produce loss of sensation over the ulnar dorsal surface of the hand (ulnar dorsal cutaneous distribution.)

Nerve Conduction Studies.

Prolonged distal latencies in motor or sensory responses, reduced amplitudes with normal sensory nerve conduction studies of the ulnar dorsal cutaneous branch. See, e.g., Reference 4 cited below.

Sensory Nerve Conduction Studies.

The sensory nerve conduction study measures the conduction of the nerve impulse along the sensory nerves. The routine method measures the conduction velocity of the large diameter sensory nerve fibers of the nerve being tested. There are two methods of obtaining sensory nerve action potentials (SNAP) orthodromic and antidromic. The orthodromic method includes recording of the sensory nerve action potential proximally and stimulating the nerve distally whereas in the antidromic method the location of the stimulating and recording electrodes is reversed. The latency and conduction velocities are identical with the orthodromic and antidromic methods if the recording and stimulating electrode positions are constant. One disadvantage of the antidromic method is that an accompanying motor response (because motor fibers are also stimulated) may distort the small SNAP. See, e.g., Reference 6 cited below.

The most commonly referenced method (See, e.g., References 2,7,8,9,10 cited below) to test ulnar dorsal sensory branch is described in the article by Joe F. Jabre, "Ulnar Nerve Lesions at the Wrist: New Technique For Recording from the Sensory Dorsal Branch of the Ulnar Nerve." *Neurology* vol. 30 (1980): 873-6. In the Jabre method, ulnar dorsal cutaneous branch is stimulated at least 5 cm proximally to the ulnar styloid. The recording electrode is placed between the fourth and fifth metacarpal bones with the reference electrode placed distally at the base of fifth digit. Under Technical Comments in the book by J.A. Liveson, "Laboratory Reference for Clinical Neurophysiology." *Oxford University Press* (1992), the author describes how to use the Jabre method. The author states that, "Stimulation may best be accomplished with the arm fully supinated, if the stimulator with angulated probe is available, pronation of the arm will be equally convenient." The book further states that, "The stimulator should be positioned between the ulnar bone and tendon of the flexor carpi ulnaris. Pressure should be exerted toward the bone. If this is not successful, some experimentation may be necessary. The stimulator can be directed laterally and pressed towards the tendon. Alternatively, it may be placed lateral to the tendon and pressed medially." The Jabre method may not be suitable for surface stimulating electrodes as it requires angulated probe and 'some experimentation'.

Another popular method is described in the article by Dae Joo Kim, M. D., "Dorsal Cutaneous Ulnar nerve Conduction." *Archives of Neurology* vol. 38 (1981): 321-22. In this method, the nerve is stimulated proximally 8-10 cm above the ulnar styloid.

In another study described in the article by A.L.C.R. Dutra De Oliveira, "Limitation of The Clinical Utility of The Ulnar Dorsal Cutaneous Sensory Nerve Action Potential", *Clinical Nerve Physiology* vol. 111 (2000): 1208-1210. The author used the method of recording sensory nerve action potential from ulnar dorsocutaneous nerve using noninsulated subdermal needle electrodes and recording from the fourth intermetacarpal space.

References.

1. Laboratory Reference for Clinical Neurophysiology" by J. A. Liveson, published by Oxford University Press in 1992, page 159.

2. Dorsal Cutaneous Ulnar Nerve Conduction. Dae Joo Kim, M. D. from Archives of Neurology, volume 38 May 1981 pages 321 and 322.

3. Limitation of The Clinical Utility of The Ulnar Dorsal Cutaneous Sensory Nerve Action Potential., by A. L. C. R. Dutra De Oliveira published in Clinical Nerve Physiology 111 2000 1208-1210.

4. Atlas of Electromyography. A. Arturo Leis, M. D., Vincente C. Trapani, M. D. Oxford University Press, pages 23-28.

5. The limitation of dorsal ulnar cutaneous sensory response in the patient with ulnar neuropathy at the elbow" by S. Venkatesh, M. D. published in Muscle and Nerve, March 1995, 18:345-347.

6. Clinical Electromyography: Nerve Conduction Studies. Shin J. Oh, M. D., pages 44-47.

7. Radial Sensory Conduction in Hand" by Henry A. Spindler, published in Archive of Physical Medicine and Rehabilitation, volume 6, 7 Nov. 1986, Pages 821 through 823.

8. Paired study of the Dorsal Cutanous Ulnar and Superficial Radial Sensory Nerves. Martin D. Hoffman, M. D. published in Archives of Physical Medicine and Rehabilitation, volume 69, August 1988, pages 591 to 594.

9. Dorsal ulnar cutaneous nerve conduction studies in asymptomatic population" by Sherry H. Young, M. D. published in Archives of Physical Medicine and Rehabilitation, volume 81, September 2000, pages 1171 through 1172.

10. Dorsal Ulnar Cutaneous Nerve Conduction, Reference Value" by Solange Garibaldi, published in Arq Neuropsiquiatr 2002; 60 (2-b): 349-352.

SUMMARY

A device and a method to stimulate and measure a response from the ulnar dorsal cutaneous nerve of a patient may include a first surface electrode to apply a stimulating signal to the ulnar dorsal cutaneous nerve, a second surface electrode to record the response from the stimulating signal after applying the stimulating signal to the ulnar dorsal cutaneous nerve, and a third surface electrode to reference the stimulating signal.

The second surface electrode may be placed over the fifth metacarpal joint, and the device may include a ground electrode positioned over the dorsal surface of the hand.

The device may include an inactive stimulating electrode positioned near to the first surface electrode.

The inactive stimulating electrode may be positioned within 3 cm of the first surface electrode, and the first electrode may be placed substantially above the tendon of the flexor carpi ulnaris muscle.

The first electrode may be placed substantially at the level of styloid, and the second surface electrode may be placed in an area supplied by the ulnar dorsal cutaneous nerve.

The first surface electrode may be placed substantially proximal to the styloid.

DETAILED DESCRIPTION

Figure 1:
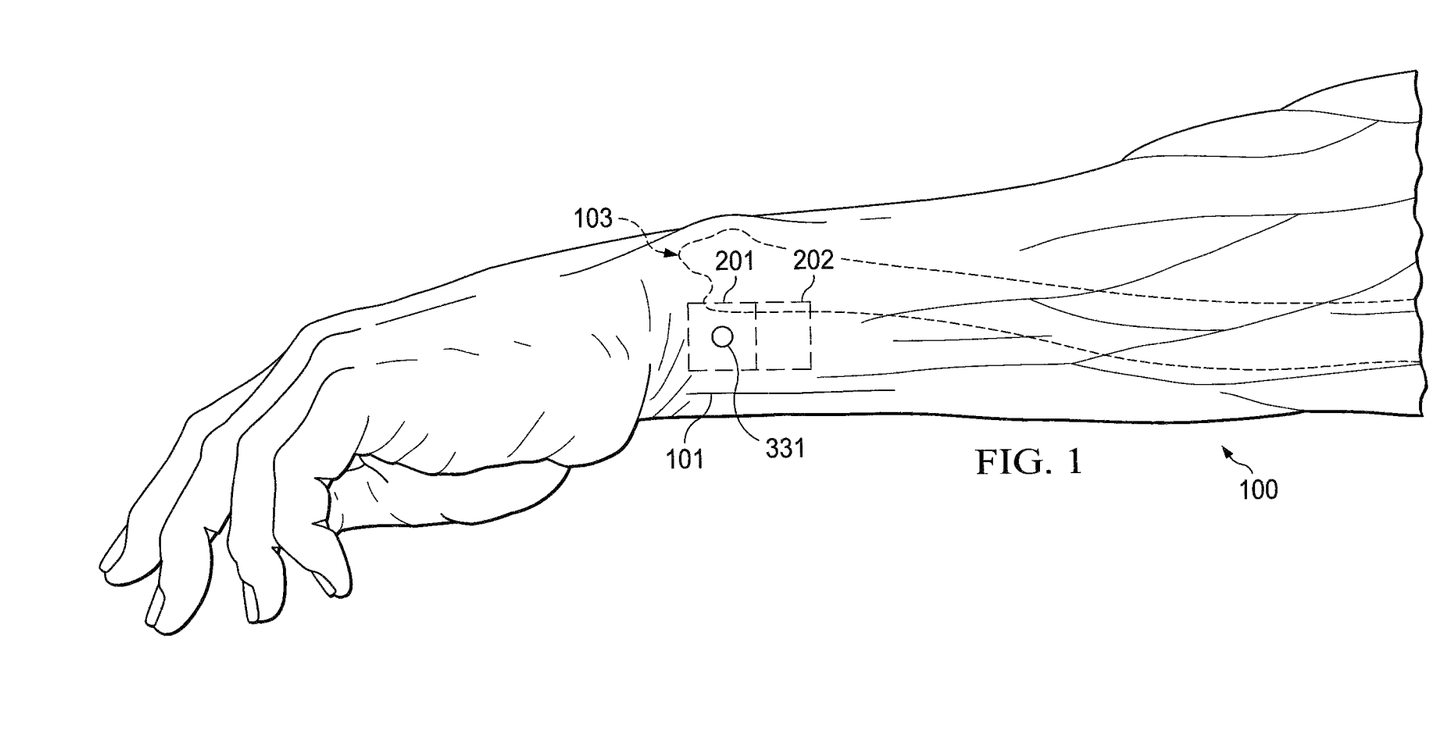
FIG. 1 illustrates a forearm to be stimulated by a stimulating electrode.
Figure 2:
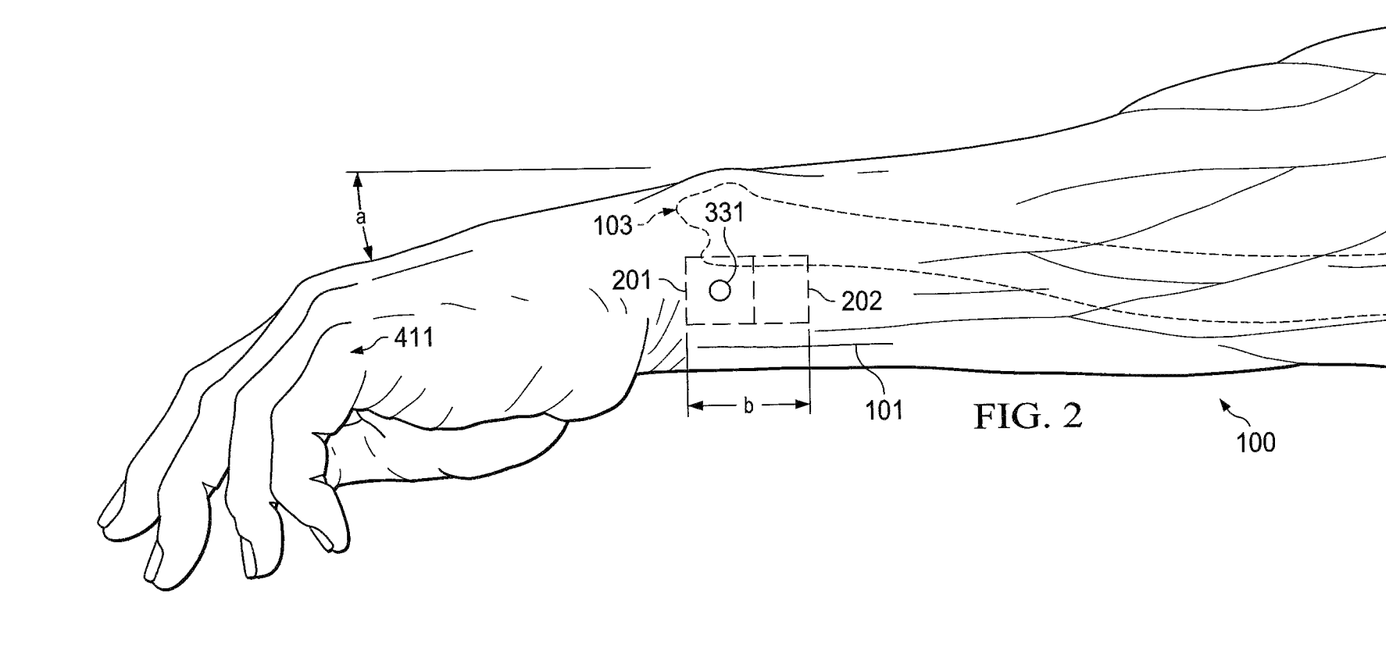
FIG. 2 illustrates a forearm to be stimulated by a stimulating electrode which may be slightly angled.

With forearm 100 substantially fully pronated as shown in FIG. 1 using surface electrodes to apply a stimulating electrical signal with a first surface electrode 331 and to record the response to the electrical signal with a second surface electrode 335, the ulnar dorsal cutaneous nerve 307 may be stimulated proximally at the level of ulnar styloid 103 or just proximal to the ulnar styloid 103, in an area 201 between the tendon of the flexor carpi ulnaris muscle inferiorly 101, and the ulna (bone) 305 and the styloid process of the ulna superiorly 103. Flexion of the wrist by an acute angle (a) (15-30 degrees) as illustrated in FIG. 2 will position the tendon of the flexor carpi ulnaris muscle 101 more inferiorly, and it will separate it from the distal ulna 305, thus increasing the area of the contact with stimulating electrode 331, and render the ulnar dorsal cutaneous nerve 307 more superficial. FIG. 2 illustrates a surface of the forearm defined generally by the rectangle 201 where the stimulating electrode 331 may stimulate the nerve 307. Alternatively, the ulnar dorsal cutaneous nerve 307 can be stimulated more proximally along its course at the substantially same position defined by the rectangle 202 which (together with the area 201) may have a length of b or substantially less than 5 cm.

Figure 3:
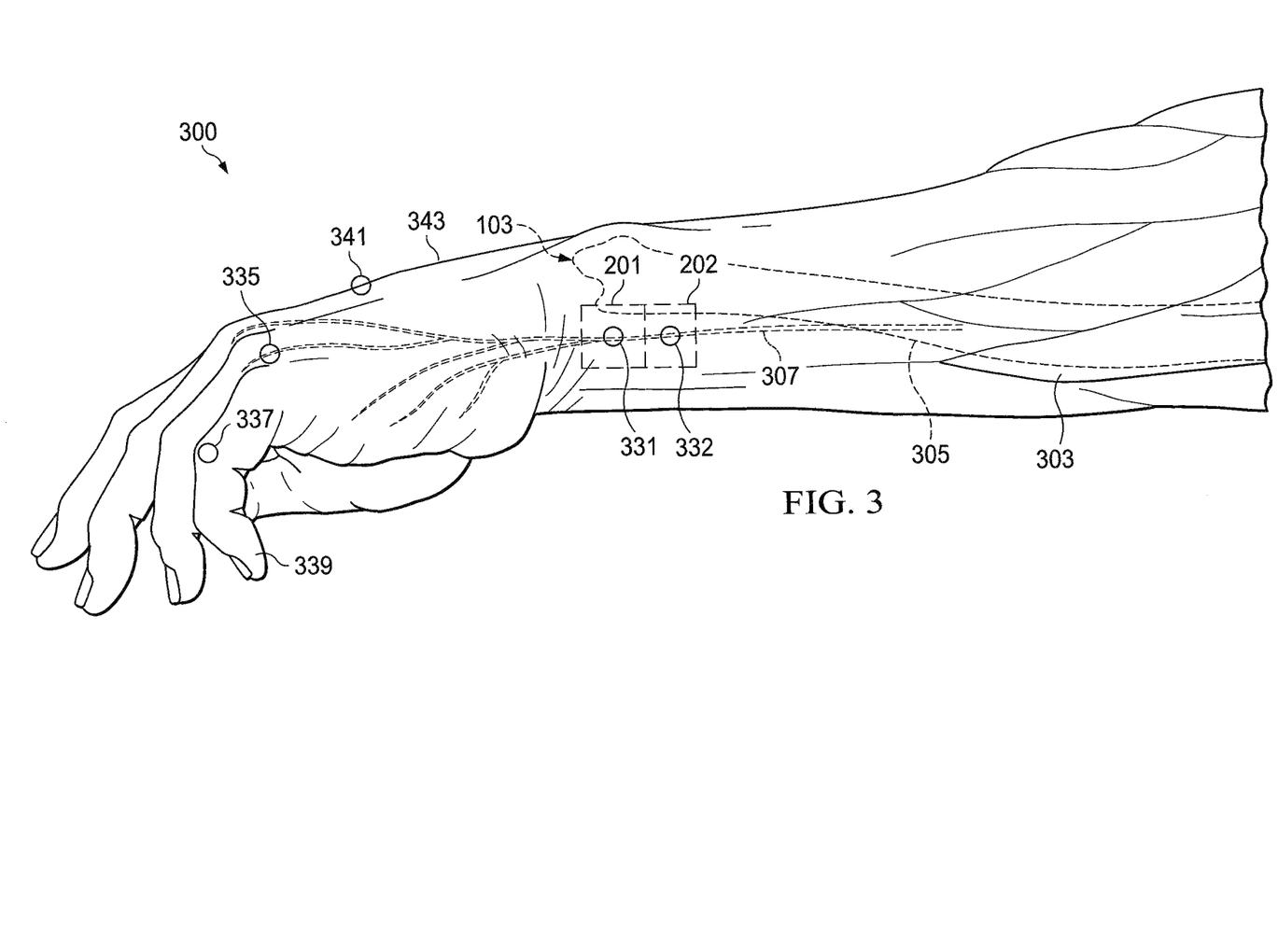
FIG. 3 illustrates a medial aspect view of the muscles, tendons, and nerves of the human forearm.
Figure 4:
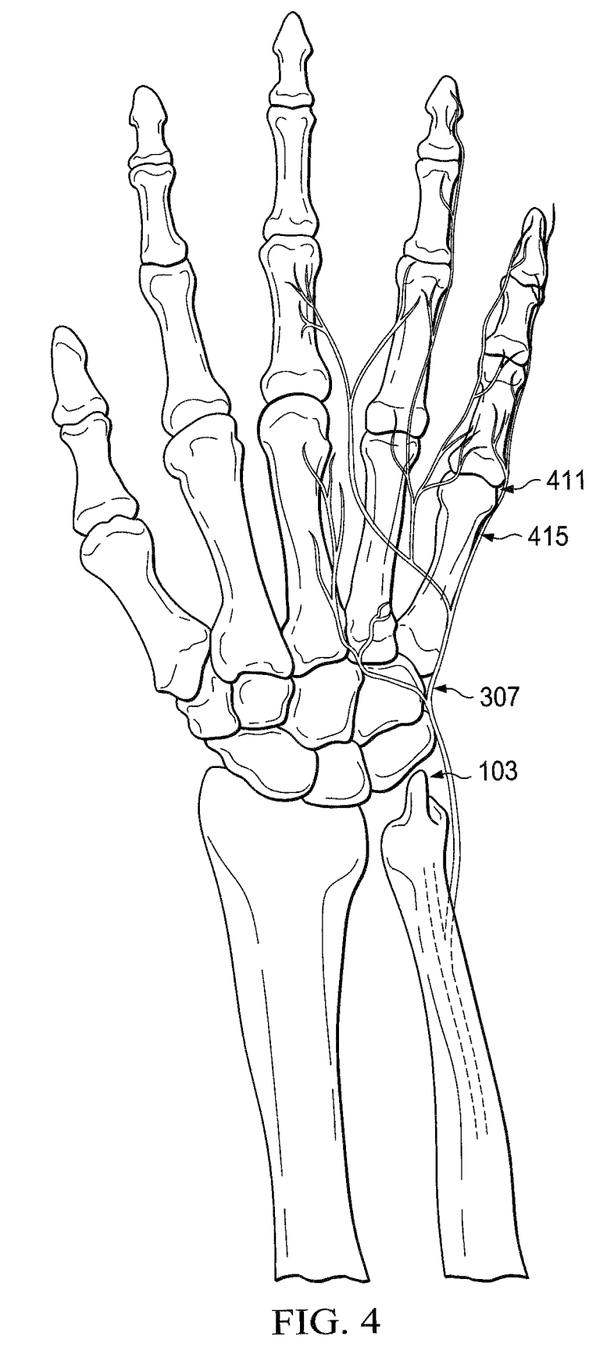
FIG. 4 illustrates the ulnar dorsal cutaneous nerve of the present invention.

Referring to FIG. 3, the active surface recording electrode 335 is placed over the distal fifth metacarpal bone 415 or fifth metacarpophalengeal joint (MCP) 411 with the reference (inactive electrode or reference to the recording electrode) 337 placed over the fifth finger 339. The ground electrode 341 may be placed over the dorsal (top) surface 343 of the hand. The distance between the center of the active recording electrode 335 and the center of the reference recording electrode 337 should be substantially 3 cm. The distance may be substantially 2 cm or 1 cm or increments of a half a centimeter between these distances. The active recording electrode 335 may be placed closer to the active stimulating electrode 331. The placement of recording electrode 337 over the distal fifth metacarpal bone 415 (or MCP joint 411) may reduce the chances of erroneous recording from the dorsal interossei muscle attached to the fifth metacarpal bone 415, and the adductor digiti minimi muscle adjacent to the distal fifth metacarpal bone 415. Alternatively, recording electrode 335 can be placed anywhere in the area supplied by the ulnar dorsal cutaneous nerve 307. The locations of the recording and stimulating electrodes may be reversed.

Figure 7:
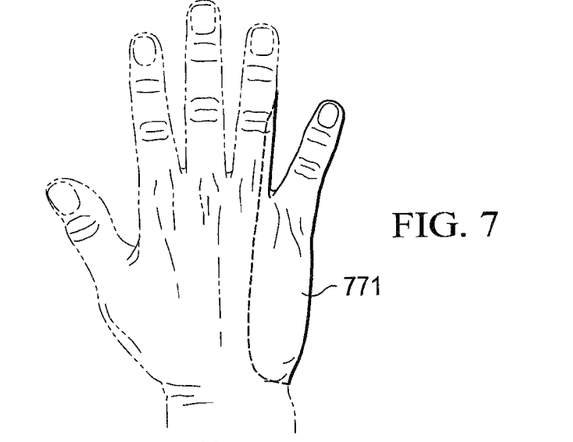
FIG. 7 illustrates a first area served by the ulnar dorsal cutaneous nerve.

FIG. 7 illustrates a top anatomical view of a first area 771 supplied by the ulnar dorsal cutaneous nerve.

Figure 8:
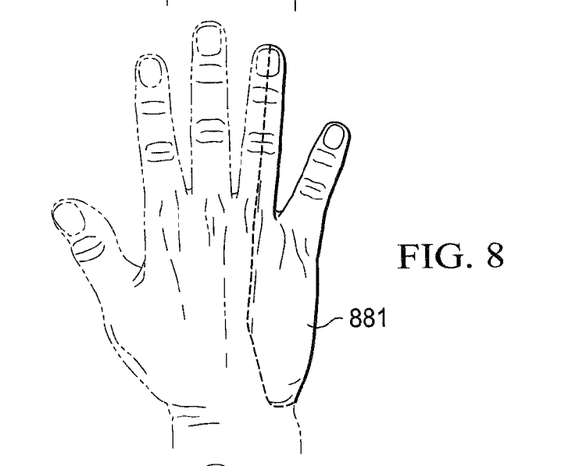
FIG. 8 illustrates a second area served by the ulnar dorsal cutaneous nerve.

FIG. 8 illustrates a top anatomical view of a second area 881 supplied by the ulnar dorsal cutaneous nerve.

Figure 9:
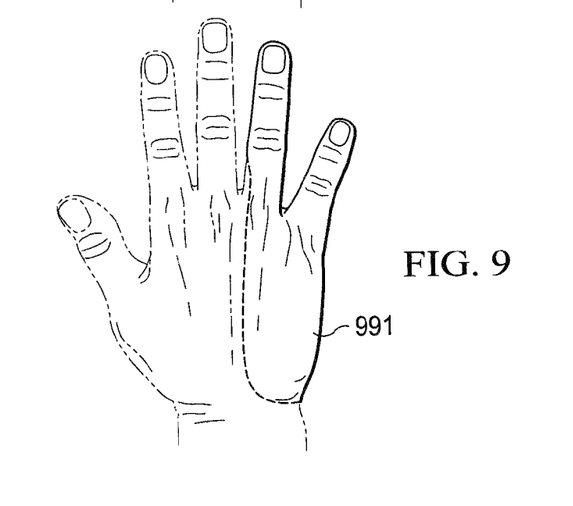
FIG. 9 illustrates a third area served by the ulnar dorsal cutaneous nerve.

FIG. 9 illustrates a top anatomical view of a third area 991 supplied by the ulnar dorsal cutaneous nerve.

The recording electrode 335 may be placed over or within the first area 771, the second area 881 and the third area 991.

The recording electrode 335 may be multiple recording electrodes 335 and positioned in combination over the first area 771, the second area 881, and the third area 991.

Proximal sensory fibers of the ulnar dorsal cutaneous nerves 307 are stimulated (antidromic sensory conduction test). The recording electrodes are switched position wise with the stimulating electrodes and vice versa. Alternatively, the distal sensory nerve fibers of the ulnar dorsal cutaneous nerve 307 could be stimulated (orthodromic sensory conduction test).

The active stimulating electrode (the cathode) 331 may be placed closer to the recording electrode. Inactive stimulating electrode 332 may be placed proximally to the active stimulating electrode 331. Stimulating electrode (active) 331 may placed above the tendon 101 of the flexor carpi ulnaris muscle 303, at the level of styloid 103, or proximal to it as seen in FIG. 3. Alternatively, the nerve can be stimulated more proximally along its course within the area 202.

The distance between the center of the active stimulating electrode 331 and the center of the inactive stimulating electrode 332 should be substantially 3 cm. The distance may be substantially 2 cm or 1 cm or increments of a half a centimeter between these distances.

A voltage range 1-200V may be used. In current controlled settings, a current range of 1-50 mA, duration of the stimulus 0.1 ms, and the filter settings: low frequency filter LFF: 20 Hz, high frequency filter HFF 3 kHz may be used.

Figure 6A:
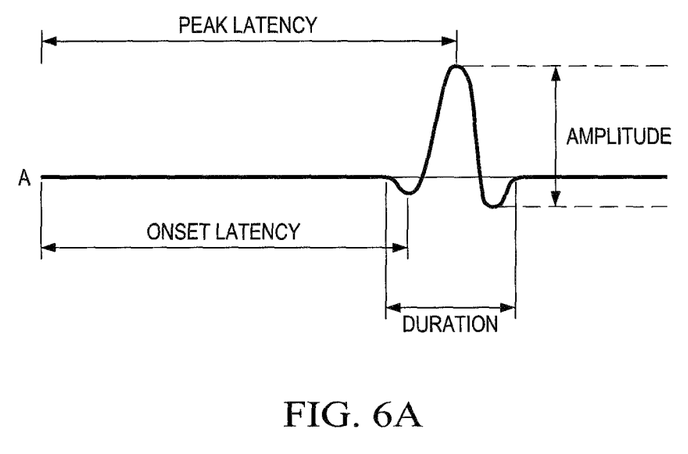
FIGS. 6a and FIG. 6b illustrate a response to a stimulation in the forearm.

Latency as shown in FIG. 6a is measured from the onset of the stimulus to the peak of the major negative deflection. Alternatively, latency may be measured from the onset of the stimulus to the initial positive peak or to the beginning of the major negative deflection as shown in FIG. 6a.

Figure 6B:
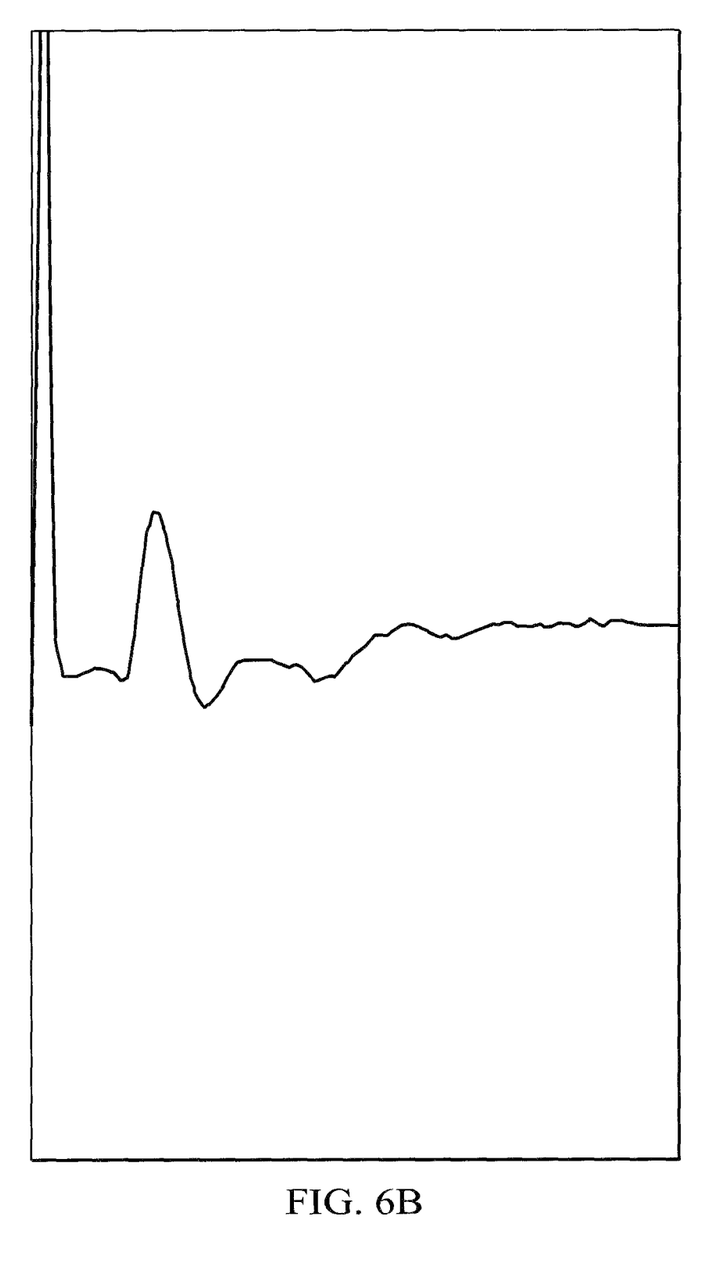

The amplitude of the sensory nerve action potential is the peak-to-peak amplitude of the above nerve potential, as measured in microvolt as shown in FIG. 6b.

Figure 5:
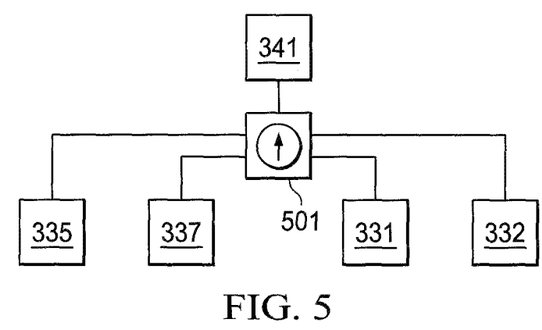
FIG. 5 illustrates a circuit of the present invention.

A signal averager 501 and/or sensory amplifier shown in FIG. 5 may be used to obtain small sensory nerve action potential (with an amplitude of less than 0.05 microvolt), which are unobtainable with routine methods.

The conduction distance of the nerve 307 is measured by surface tape measurement from the center of the active stimulating electrode to the center of the active recording electrode. It is expressed in millimeters.

Nerve conduction velocity is calculated by dividing the conduction distance (mm) by the latency (ms). If the distance between the stimulating and recording electrodes is standardized, only the latency may be used.

If required, nerve conduction velocity is adjusted to standard temperature.

Nerve conduction velocities, latencies, amplitudes, duration, and shape of the sensory nerve action potentials are compared with normal conduction velocities, latencies, amplitudes duration and shape in order to determine abnormalities such as: prolonged latencies, diminished sensory nerve action potential amplitudes, prolonged sensory nerve action potential durations, reduced conduction velocities, or absent responses all together.

While the present invention has been described in connection with the exemplary embodiments of the various figures, it is not limited thereto and it is to be understood that other similar embodiments may be used or modifications and additions may be made to the described embodiments for performing the same function of the present invention without deviating therefrom. Therefore, the present invention should not be limited to any single embodiment, but rather should be construed in breadth and scope in accordance with the appended claims. Also, the appended claims should be construed to include other variants and embodiments of the invention, which may be made by those skilled in the art without departing from the true spirit and scope of the present invention.

The invention claimed is:

1. A method to stimulate and measure a response from an ulnar dorsal cutaneous nerve of a hand, comprising the steps of:
   positioning a first surface electrode in a medial area of a forearm of the hand between a tendon of a flexor carpi ulnaris muscle and a styloid process of an ulna bone during flexion of a wrist of the hand at an acute angle with respect to the forearm to increase contact area with the first surface electrode;
   positioning a second surface electrode on a dorsal surface of the hand over a fifth metacarpal joint;
   using the first surface electrode to apply a stimulating signal to the ulnar dorsal cutaneous nerve;
   using the second surface electrode to record the response from the stimulating signal after applying the stimulating signal to the ulnar dorsal cutaneous nerve; and
   using a third surface electrode to reference the stimulating signal.

2. A method to stimulate and measure a response from the ulnar dorsal cutaneous nerve of a hand as in claim 1, wherein the method includes the step of positioning a ground electrode over the dorsal surface of the hand.

3. A method to stimulate and measure a response from the ulnar dorsal cutaneous nerve of a hand as in claim 1, wherein the method includes the step of positioning an inactive stimulating electrode near to the first surface electrode.

4. A method to stimulate and measure a response from the ulnar dorsal cutaneous nerve of a hand as in claim 3, wherein the method includes the step of positioning the inactive stimulating electrode within 3 cm of the first surface electrode.

5. A method to stimulate and measure a response from the ulnar dorsal cutaneous nerve of a hand as in claim 1, wherein the flexion of the wrist at the acute angle with respect to the forearm renders the ulnar dorsal cutaneous nerve more superficial.

6. A method to stimulate and measure a response from the ulnar dorsal cutaneous nerve of a hand as in claim 5, wherein the first surface electrode is placed substantially at the level of styloid.

7. A method to stimulate and measure a response from the ulnar dorsal cutaneous nerve of a hand as in claim 5, wherein the first surface electrode is placed substantially proximal to styloid.

8. A method to stimulate and measure a response from the ulnar dorsal cutaneous nerve of a hand as in claim 1, wherein the second surface electrode is placed in an area supplied by the ulnar dorsal cutaneous nerve.

9. A method to stimulate and measure a response from the ulnar dorsal cutaneous nerve of a hand as in claim 1, wherein the flexion of the wrist at the acute angle with respect to the forearm is in a range of 1 to 60 degrees.

10. A method to stimulate and measure a response from the ulnar dorsal cutaneous nerve of a hand as in claim 1, wherein the first surface electrode and the second surface electrode are reversed in position.

* * * * *